(12) United States Patent
Li et al.

(10) Patent No.: US 9,241,774 B2
(45) Date of Patent: Jan. 26, 2016

(54) PATTERNED DENTAL POSITIONING APPLIANCE

(75) Inventors: Chunhua Li, Cupertino, CA (US); Yan Chen, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 281 days.

(21) Appl. No.: 12/771,690

(22) Filed: Apr. 30, 2010

(65) Prior Publication Data
US 2011/0269091 A1 Nov. 3, 2011

(51) Int. Cl.
*A61C 13/00* (2006.01)
*A61C 7/08* (2006.01)

(52) U.S. Cl.
CPC ............. *A61C 7/08* (2013.01); *Y10T 29/49568* (2015.01)

(58) Field of Classification Search
CPC ............ A61C 7/08; A61C 7/002; A61C 7/10; A61C 7/12; A61C 7/00
USPC ...................................... 264/16–20
See application file for complete search history.

(56) References Cited

U.S. PATENT DOCUMENTS

| 4,439,154 | A | * | 3/1984 | Mayclin ........................ 433/229 |
| 4,591,341 | A | * | 5/1986 | Andrews ........................... 433/6 |
| 4,983,334 | A | * | 1/1991 | Adell ............................... 264/16 |
| 5,055,039 | A | * | 10/1991 | Abbatte et al. .................. 433/24 |
| 5,083,919 | A | * | 1/1992 | Quach ............................... 433/6 |
| 5,975,906 | A | * | 11/1999 | Knutson ........................ 433/226 |
| 6,309,215 | B1 | * | 10/2001 | Phan et al. ...................... 433/24 |
| 2010/0086890 | A1 | | 4/2010 | Kuo |

FOREIGN PATENT DOCUMENTS

| WO | 0032131 | 6/2000 |
| WO | 2008115654 | 9/2008 |

OTHER PUBLICATIONS

International Search Report corresponding to International Patent Application PCT/IB2011/000904, mailing date Dec. 1, 2011.

* cited by examiner

*Primary Examiner* — Stella Yi
(74) *Attorney, Agent, or Firm* — Brooks, Cameron & Huebsch, PLLC (57) ABSTRACT

Embodiments are provided for a patterned dental positioning appliance. One method embodiment includes receiving a dental mold of a patient's dentition, applying a pattern to a portion of the dental mold, and applying a material to the dental mold to form the removable dental positioning appliance that includes either the pattern on the portion of the dental mold or an inverse thereof.

10 Claims, 5 Drawing Sheets

PATTERNED DENTAL POSITIONING APPLIANCE

BACKGROUND

The present disclosure is related generally to the field of dental treatment. More particularly, the present disclosure is related to methods, devices, and systems for creating and utilizing dental positioning appliances.

Many dental treatments involve repositioning misaligned teeth and changing bite configurations for improved cosmetic appearance and dental function. Orthodontic repositioning can be accomplished, for example, by applying controlled forces to one or more teeth over a period of time.

An example of orthodontic repositioning that can occur can be through a dental process that uses one or more positioning appliances for realigning teeth. Such appliances may utilize a shell of material having resilient properties, referred to as an "aligner" that generally conforms to a patient's teeth but is slightly out of alignment with the initial tooth configuration.

Placement of such an appliance over the teeth can provide controlled forces in specific locations to gradually move the teeth into a new configuration. Repetition of this process with successive appliances in progressive configurations can move the teeth through a series of intermediate arrangements to a final desired arrangement.

Such systems typically utilize materials, such as thermoplastic polyurethane, polyester, and co-polyester, among others, that are thin, light weight, and/or transparent to provide as a set of appliances that can be used serially such that as the teeth move, a new appliance can be implemented to further move the teeth.

These materials are applied via a rapid prototyping or other construction process in generally uniform layers over a mold or built up without a mold to an aligner shape having a substantially uniform thickness. In some applications the forces provided by such uniform thickness structure may not provide a suitable amount of force (i.e., too much or too little force) in magnitude, direction, and/or duration.

DETAILED DESCRIPTION

Embodiments of the present disclosure include device, system, and method embodiments for creating and utilizing patterned dental positioning appliances. For example, one method embodiment for forming a removable dental positioning appliance includes receiving a dental mold of a patient's dentition, applying a pattern to a portion of the dental mold, and applying a material to the dental mold to form the removable dental positioning appliance that includes either the pattern on the portion of the dental mold or an inverse thereof.

The patterns on the dental positioning appliances can be beneficial, for example, in that controlling the direction, duration, and/or magnitude of the force exerted by a particular portion of a dental positioning appliance on one or more teeth can be improved versus appliances without patterning thereon. If only patterned on a portion or patterned with multiple patterns, controlling the direction, duration, and/or magnitude of the force exerted by a particular portion of a dental positioning appliance on one or more teeth can be different from one portion of an appliance to another based on whether a pattern is utilized and/or the structure and/or orientation of the pattern, among other benefits.

Additionally, in some embodiments, a pattern or portion thereof can provide force to a particular position on a tooth and/or can be used to provide additional contact strength for the appliance with the tooth.

Data regarding a patient's tooth layout can be obtained manually or in an automated manner in a number of ways. For example, with computer-aided tooth treatment systems, an initial digital data set (IDDS) representing an initial tooth arrangement may be obtained.

This IDDS may be also obtained in a variety of ways. For example, the patient's teeth may imaged to obtain data using X-rays, three-dimensional X-rays, computer-aided tomographic images or data sets, magnetic resonance images, and/or other imaging techniques.

In some situations, a plaster cast and/or mold of the patient's teeth may be scanned using a laser scanner or other range acquisition system to produce the IDDS. The data set produced by the range acquisition system may be converted to other formats to be compatible with the software which is used for manipulating images within the data set, as described herein. The data set can be used to create a series of aligners used to move teeth though successive arrangements.

In the embodiments of the present disclosure, one or more patterns can be added to one or more physical models or to digital models to facilitate the fabrication of one or more patterned appliances.

Figure 1:
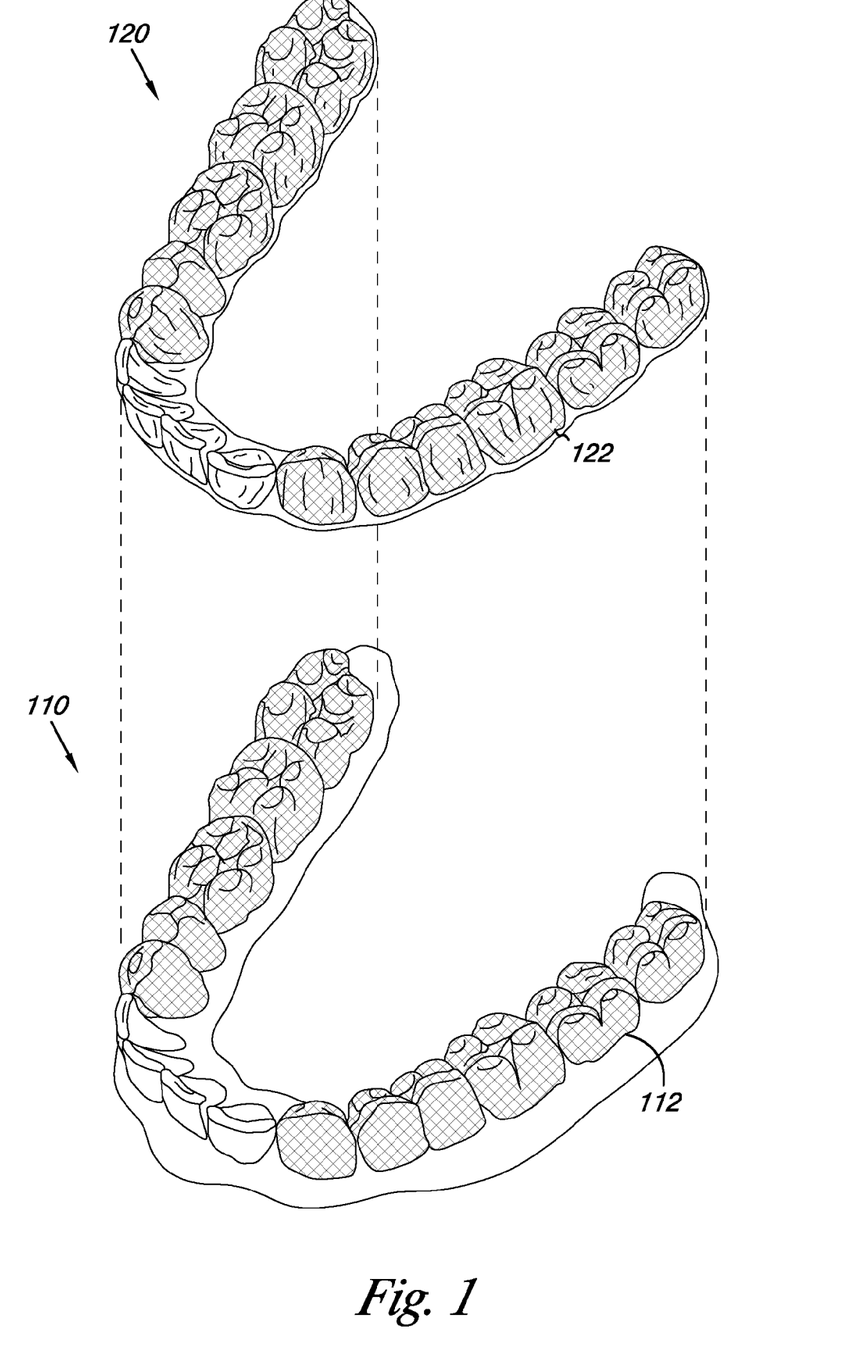
FIG. 1 illustrates a dental mold that includes a pattern and a dental positioning appliance that includes the pattern according to an embodiment of the present disclosure.

For example, the embodiment in FIG. 1, illustrates a dental mold that includes a pattern and a dental positioning appliance that includes the pattern according to an embodiment of the present disclosure. In the embodiment illustrated in FIG. 1, dental mold 110 includes a pattern 112 thereon and a dental positioning appliance 120, formed based on the mold 110, includes a similar pattern 122. The formation of such patterns will be discussed in more detail below.

A dental mold can be created in a variety of different ways. For example, the dental mold 110 can be created based on data obtained from a scan of the patient's teeth or an original mold made of the patient's teeth, as discussed above.

One or more patterns can be provided on the mold and can be provided in a variety of ways. For example, any pattern shape that can provide additional support to a portion of the appliance and/or can provide a force component to a portion of the appliance could be beneficial in various embodiments. Pattern elements can, for example, be straight lines, curved lines, uniform or non-uniform circumference bumps, or other shapes that can be utilized to impart force, among other uses.

The pattern 112 on the dental mold 110 can be formed from a material that is placed, either temporarily or permanently, on the dental mold 110. The pattern 112 can also be formed on the dental mold when building the dental mold from data using a method such as rapid prototyping, among other processes. In such embodiments, the pattern can be formed of materials that are the same as those used to create the mold and/or from different materials.

In some applications, such a process can be beneficial for a number of reasons. For example, the appliance with patterns will be a generally unitary body (e.g., formed from one material or having the patterned material integrated into and/or onto the appliance body as it is being fabricated) which may be more resistant to wear and tear and/or may be capable of providing more force than non-unitary appliances due to the general unitary nature of the appliance body.

The patterns on the dental mold can include any configuration and multiple patterns can be utilized on the dental mold as will be discussed in more detail below. For example, a first tooth can include a first pattern and a second tooth can include a second pattern or no pattern, additionally, one or more portions of the aligner that cover an area between teeth may have a pattern.

The patterned dental positioning appliance 120 can be formed by placing appliance material over a dental mold 110 creating an appliance via, for example a thermal forming process, thereby forming the one or more inner cavities of the dental appliance that will be in contact with the teeth of the patient with the inverse shape of the dental mold 110.

In various embodiments, a pattern 122 can be on an inner surface of the dental positioning appliance 120. In some embodiments, the outer surface of the appliance does not have pattern 122 thereon. This may be beneficial, for example, in providing a surface that feels more palatable to some patients and/or that is less visible when viewed by others.

In various embodiments, the pattern 122 on the dental positioning appliance 120 can vary in direction, intensity, and/or location of the one or more forces exerted by the appliance 120 on one or more teeth when placed over a patient's teeth. Such changes to the forces exerted and design of appliances based on such considerations will be discussed in more detail below.

Figure 2:
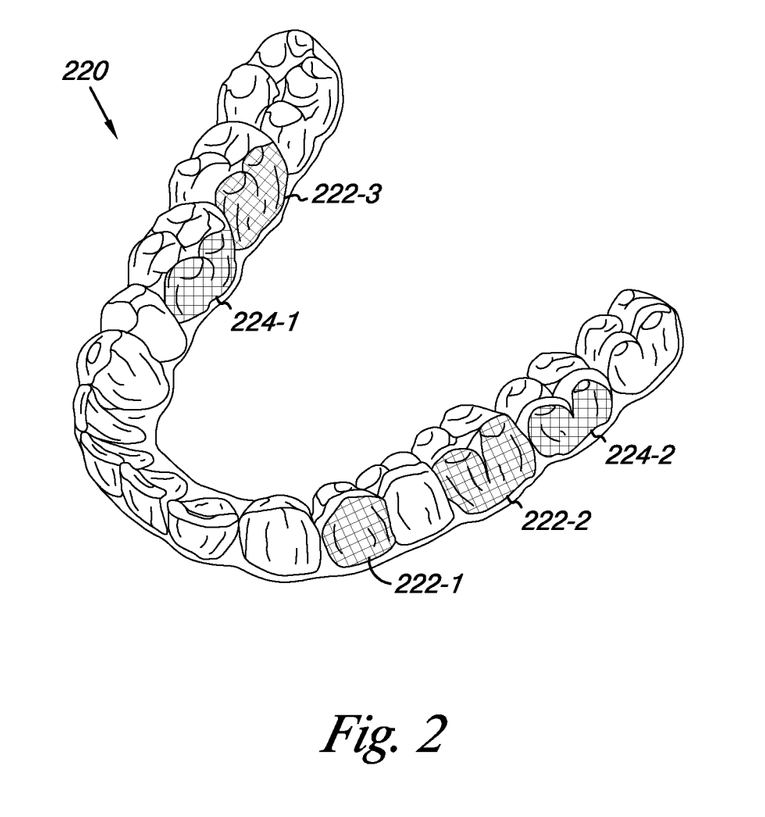
FIG. 2 illustrates a dental positioning appliance that includes a number of patterns according to an embodiment of the present disclosure.

FIG. 2 illustrates a dental positioning appliance that includes a number of patterns according to an embodiment of the present disclosure. The dental positioning appliance 220 in FIG. 2 includes a first pattern on a first tooth 222-1, a second tooth 222-2, and a third tooth 222-3. In the embodiment of FIG. 2, the dental positioning appliance 220 also includes a second pattern on a fourth tooth 224-1 and a fifth tooth 224-2.

In FIG. 2, the first pattern on the first tooth 222-1, second tooth 222-2, and third tooth 222-3 can be used to exert a force in a certain direction and/or provide a magnitude of one or more force components that is different than the force exerted by the non-patterned portions of the appliance and/or the portions having the second pattern on the fourth tooth 224-1 and fifth tooth 224-2.

Dental positioning appliances, such as that shown in FIG. 2, can be created using a rapid prototyping process. In such processes, data of a patient's teeth is often used to form a dental positioning appliance that can be utilized to treat a patient's orthodontic condition. Rapid prototyping processes used to create the dental positioning appliance can be utilized to create the patterns while the appliance is built up during the rapid prototyping process.

Patterns can be created having varying degrees of magnitude of force exerted by the dental positioning appliance and/or can isolate forces to certain areas of a patient's teeth in certain directions, among other benefits.

In various embodiments, a number of patterns can be utilized to strengthen portions of or the entire dental positioning appliance, thus reducing dimensional deformation of the aligner and/or fatigue. This can increase the useful life of an appliance and/or can allow for longer treatment periods with the same appliance, in some instances. In various embodiments, a pattern can be used as a source identifier and/or an ornamental design, among other uses. These features can be in addition to or instead of the structural advantages described in some embodiments herein.

Removable dental positioning appliances have cavity geometries shaped to receive and reposition one or more teeth from a first arrangement to a successive arrangement. In some embodiments, a portion of the appliance can include a pattern in at least one cavity geometry that is different from another cavity geometry.

Removable dental positioning appliances can have varying dimensions and/or thicknesses at various portions and/or cavity geometries of an appliance. The varying dimensions and/or thickness at various portions of an appliance can include a number of patterns that can affect the direction and/or magnitude of force exerted by the dental positioning appliance.

The pattern on a portion of the appliance can be designed to improve and/or reduce the application of a force in one or more directions on a tooth when the appliance is placed over a user's teeth. In one or more embodiments, the pattern can be on a portion of a textile material that is attached to an inner surface of the appliance.

The appliance can include a first pattern with a first size, shape, and/or material on at least a portion of a first cavity geometry shaped to receive and reposition a first tooth and a second pattern with a second size, shape, and/or material on at least a portion of a second cavity geometry shaped to receive and reposition a second tooth. Those of ordinary skill in the art will understand that any suitable pattern may be used based upon the desired force result.

Figure 3:
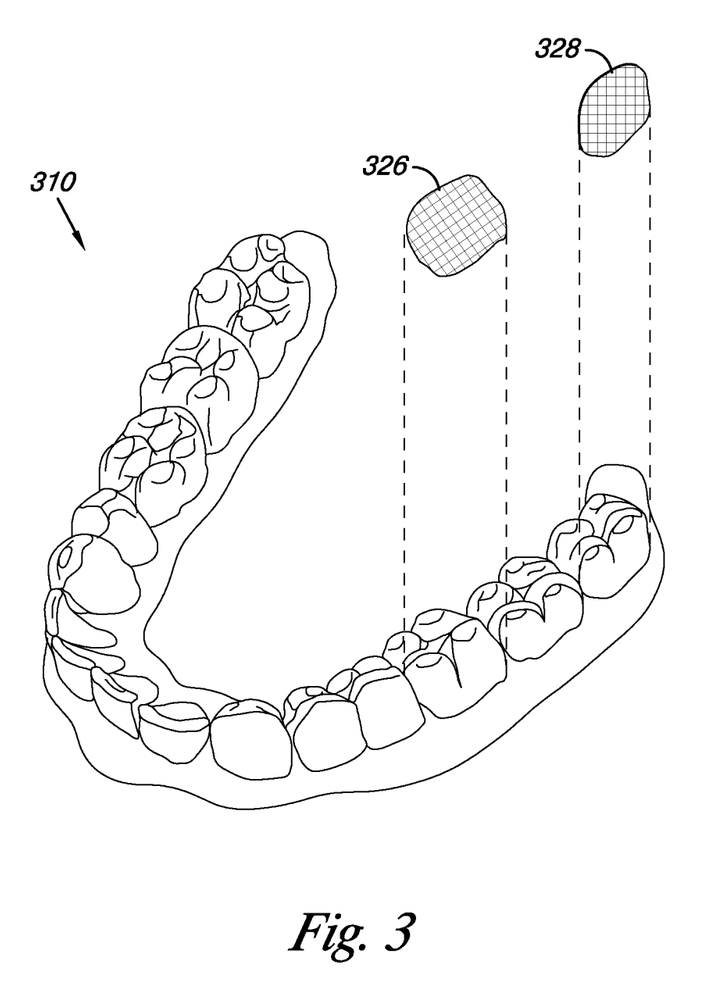
FIG. 3 illustrates a dental mold and a multiple patterned material pieces used to create patterns on the dental mold according to an embodiment of the present disclosure.

FIG. 3 illustrates a dental mold and a multiple patterned material pieces used to create patterns on the dental mold according to an embodiment of the present disclosure. As discussed above, dental mold 310 can be created from a mold of a patient's dentition or can be formed by a method such as rapid prototyping using data obtained from a scan of the patient's dentition. As illustrated in FIG. 3, the patterns can be formed in pieces of material 326 and 328 and placed on the dental mold.

In such embodiments, materials with various patterns can be cut to fit a desired number of model teeth on the dental mold and placed on the desired teeth of the mold. The dental mold 310 can then be scanned and used in a thermal forming process, material can be laid over the mold, or another suitable process can be used to create a patterned dental positioning appliance that includes the pattern of the material or an inverse thereof on the desired teeth openings of the dental positioning appliance.

Figure 4:
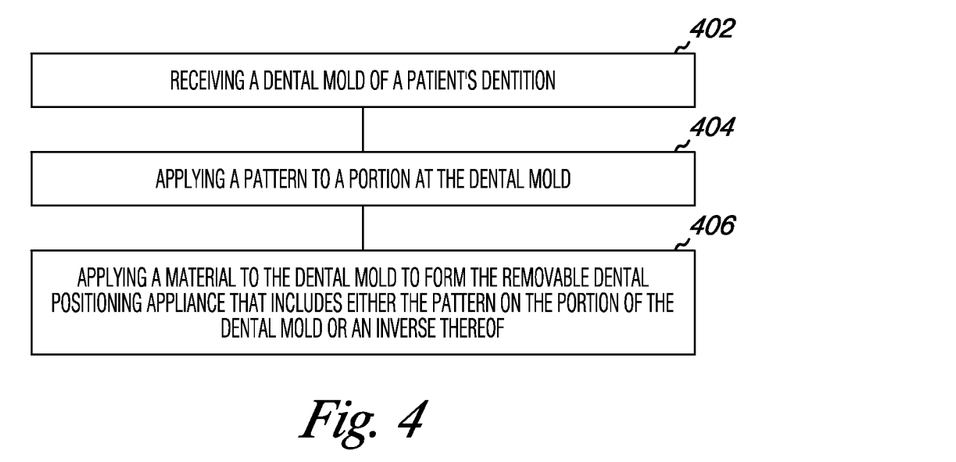
FIG. 4 illustrates a method of forming a removable dental positioning appliance according to an embodiment of the present disclosure.

FIG. 4 illustrates a method of forming a removable dental positioning appliance according to an embodiment of the present disclosure. In FIG. 4, the method of forming the removable dental positioning appliance includes receiving a dental mold of a patient's dentition 402. The dental mold can be created from data obtained during a scan of a patient's dentition and/or from data obtained during a scan of a mold of a patient's dentition.

The method also includes applying a pattern to a portion of the dental mold 404 and applying a material to the dental mold to form the removable dental positioning appliance that includes either the pattern on the portion of the dental mold or an inverse thereof 406. In some embodiments, applying the pattern on a portion of the dental mold includes building the pattern on the dental mold by adding material to or removing material from the dental mold. In some embodiments, applying the pattern on a portion of the dental mold includes applying a pre-patterned material to the dental mold. Some embodiments can include releasing the pre-patterned material from the removable dental positioning appliance after the material forming the dental positioning appliance is applied to the dental mold.

In various embodiments, a system of removable dental positioning appliances can include a number of successive removable dental positioning appliances wherein each of the number of successive removable dental positioning appliances can exert a force on one or more patient's teeth to move the patient's teeth an incremental amount. The inner surface of at least one of the number of successive removable dental positioning appliances can include one or more patterns that is designed to focus a contact force imparted on the patient's teeth at particular locations corresponding to one more features of the one or more patterns.

In one or more embodiments, each of the number of successive removable dental positioning appliances can include one or more patterns at least one of these patterns being a mesh pattern. The mesh pattern can be used to impart a contact force in the surface of the tooth at an intersection of two mesh ligaments forming the mesh structure. In one or more embodiments, each of the number of successive removable dental positioning appliances can include one or more patterns with raised shapes that impart a contact force.

Figure 5:
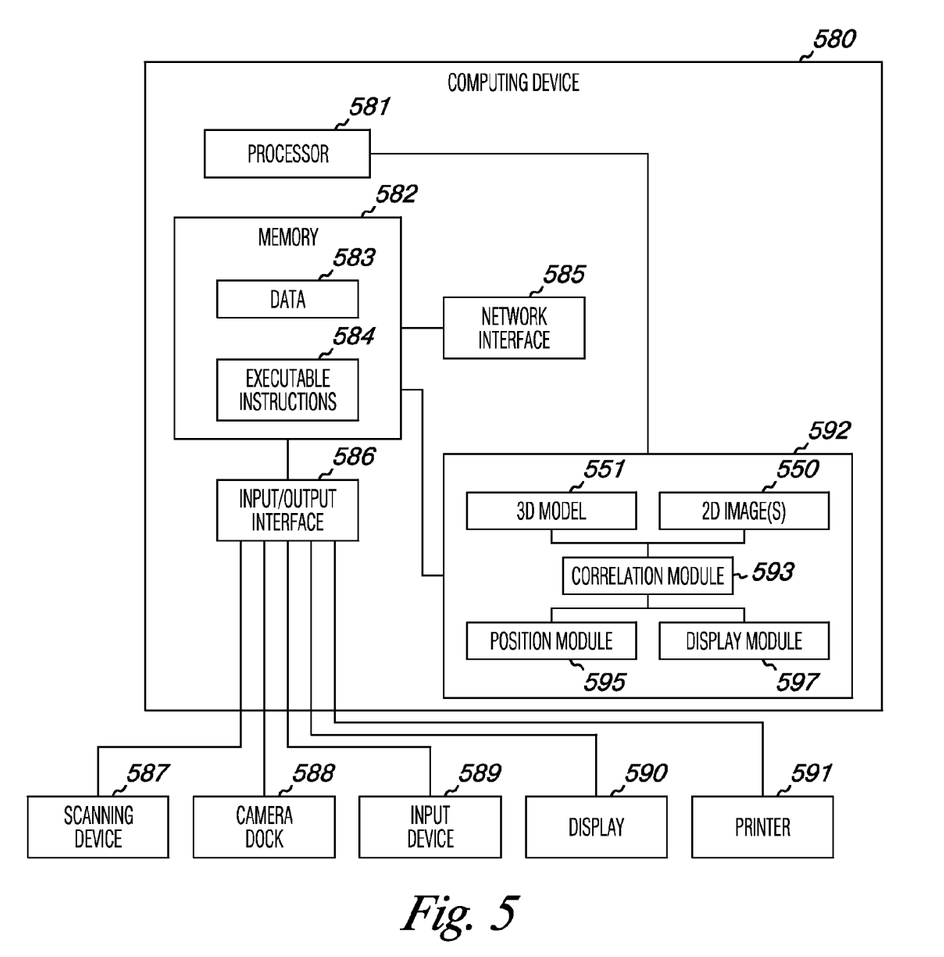
FIG. 5 illustrates a system for virtual dental modeling according to an embodiment of the present disclosure.

FIG. 5 illustrates a system for virtual dental modeling according to one or more embodiments of the present disclosure. In the system illustrated in FIG. 5, the system includes a computing device 580 having a number of components coupled thereto.

The computing device 580 includes a processor 581 and memory 582. The memory can include various types of information including data 583 and executable instructions 584 as discussed herein.

Memory and/or the processor may be located on the computing device 580 and/or associated with the device via a computing network in some embodiments. As such, as illustrated in the embodiment of FIG. 5, a system can include a network interface 585. Such an interface can allow for processing on another networked computing device or such devices can be used to obtain information about the patient or executable instructions for use with various embodiments provided herein.

As illustrated in the embodiment of FIG. 5, a system can include one or more input and/or output interfaces 586. Such interfaces can be used to connect the computing device with one or more input or output devices.

For example, in the embodiment illustrated in FIG. 5, the system includes connectivity to a scanning device 587, a camera dock 588, an input device 589 (e.g., a keyboard, mouse, etc.), a display device 590 (e.g., a monitor), and a printer 591. The input/output interface 586 can receive data, storable in the data storage device (e.g., memory 582), representing the virtual dental model corresponding to the patient's upper jaw and the patient's lower jaw.

In some embodiments, the scanning device 587 can be configured to scan a physical mold of a patient's upper jaw and a physical mold of a patient's lower jaw. In one or more embodiments, the scanning device 587 can be configured to scan the patient's upper and/or lower jaws directly. The scanning device can be configured to input data to the correlation module 593.

The camera dock 588 can receive an input from an imaging device (e.g., a 2D imaging device) such as a digital camera or a printed photograph scanner. The input from the imaging device can be stored in the data storage device 582. The input from the imaging device can represent a photograph, for example, of a patient's upper jaw and the patient's lower jaw in a bite configuration. The input from the imaging device can include data representing a point marked on the photograph.

The processor 581 can be configured to provide a visual indication of a photograph and/or a virtual dental model on the display 590 (e.g., on a GUI running on the processor 581 and visible on the display 590). The GUI can be configured to allow a user to mark one or more points on the photograph and/or the virtual dental model. Such points marked via the GUI can be received by the processor 581 as data and/or stored in memory 582. The processor 581 can be configured to map points marked on the photograph to the virtual dental model and to provide a visual indication of one or both on the display 590.

Such connectivity can allow for the input and/or output of image information (e.g., scanned images or digital pictures, etc.) or instructions (e.g., input via keyboard) among other types of information. Although some embodiments may be distributed among various computing devices within one or more networks, such systems as illustrated in FIG. 5 can be beneficial in allowing for the capture, calculation, and/or analysis of information discussed herein.

The processor 581, in association with the data storage device 582, can be associated with data and/or application modules 592. The processor 581, in association with the data storage device 582, can store and/or utilize data and/or execute instructions to provide a number of application modules for virtual dental modeling on a computing device.

Such data can include two dimensional and/or three dimensional (2D and 3D) virtual modeling data such as the data utilized to create the virtual dental model 551 described herein (e.g., including a first jaw and a second jaw) and a number of 2D images 550 (e.g., of a patient's jaws corresponding to the jaws of the 3D virtual dental model 551). Such application modules can include a correlation module 593, a position module 595, and/or a display module 597.

The correlation module 593 can be configured to correlate one or more 2D images 550 with the 3D virtual dental model 551. For example, the correlation module 593 can be configured to transform points marked on the one or more 2D images 550 from a coordinate system associated therewith to a coordinate system associated with the 3D virtual dental model 551.

The position module 595 can be associated with the correlation module 593 and configured to determine the position of the teeth in the virtual dental model based on output of the correlation module 593. That is, the position module 595 can provide the relative positioning and movement simulation of teeth of the 3D virtual dental model described herein. In one or more embodiments, the position module 595 can be configured to use points marked on the 2D image and transformed from 2D to 3D coordinate systems as targets of movement for corresponding points marked on the 3D virtual dental model.

According to one or more embodiments, the position module 595 can be configured to simulate of movement of a number of teeth with respect to a prior position of teeth of the virtual dental model based on an output of the correlation module 593. For example, such output of the correlation module can include transformations of points marked on a plurality of 2D images from a coordinate system associated therewith to a coordinate system associated with the 3D virtual dental model.

The display module 597 can be associated with the correlation module 593 and the position module 595. The display module 597 can be configured to provide a display of the 3D virtual dental model and/or the 2D image of the patient's dentition. For example, the display module can provide a display of a simulation of anatomical movement output from the position module 595. The display module 597 can provide such a display via display 590.

Functionality of the display module 597 (e.g., via a GUI) can allow a user to mark points on the 2D image and corresponding points on the 3D virtual dental model. The correspondence of points marked on the 2D image and the 3D virtual dental model can be improved (e.g., deviation between corresponding points can be reduced) according to embodiments in which the display module 597 provides a simultaneous display of the 2D image and the 3D virtual dental model.

As discussed with respect to FIG. 5, some embodiments of the present disclosure also include a computing device including a processor, memory connected to the processor, and computing device executable instructions storable in the memory and executable by the processor. For example, in some embodiments, the device can create a removable dental positioning appliance by receiving a dental mold of a patient's dentition, applying a pattern to a portion of the dental mold, and applying a material to the dental mold to form the removable dental positioning appliance that includes either the pattern on the portion of the dental mold or an inverse thereof. Such functions can be provided by executable instructions stored in memory and executable by a logic circuit such as a processor.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method of forming a removable dental positioning appliance, comprising:
applying a pattern to a portion of a dental mold of a patient's dentition corresponding to one or more of the patient's teeth, wherein applying the pattern to the portion of the dental mold includes applying a pre-patterned material to the dental mold;
applying a material to the dental mold including the portion having the pattern to form the removable dental positioning appliance, comprising a shell including a plurality of inner cavities to contact the patient's teeth, such that the appliance includes either the pattern or an inverse thereof on a surface of the inner cavities, the pattern or the inverse thereof being designed to affect application of a force from the removable dental positioning appliance directly on a tooth of the patient; and
releasing the pre-patterned material from the removable dental positioning appliance after the material forming the dental positioning appliance is applied to the dental mold.

2. The method of claim 1, wherein applying the pattern includes providing a first pattern on a first portion of the dental mold and a second pattern on a second portion of the dental mold.

3. The method of claim 1, wherein applying the pattern to the portion of the dental mold includes applying the pattern formed of repeated elements of one or more of straight lines, curved lines, uniform circumference bumps, and non-uniform circumference bumps.

4. The method of claim 1, wherein applying a material to the dental mold to form the removable dental positioning appliance includes applying the material such that an outer surface of the shell does not include either the pattern or an inverse thereof.

5. The method of claim 1, wherein applying the material comprises applying one material to the dental mold including the portion having the pattern to form the removable dental positioning appliance such that the appliance includes either the pattern or the inverse thereof on the surface of the inner cavities and such that the appliance with the pattern or the inverse thereof is a unitary body formed from the one material.

6. A method of forming a removable dental positioning appliance, comprising:
applying a pattern to a portion of a dental mold of a patient's dentition corresponding to one or more of the patient's teeth, wherein applying the pattern to the portion of the dental mold includes building the pattern on the dental mold by removing material from the dental mold; and
applying a material to the dental mold including the portion having the pattern to form the removable dental positioning appliance, comprising a shell including a plurality of inner cavities to contact the patient's teeth, such that the appliance includes either the pattern or an inverse thereof on a surface of the inner cavities, the pattern or the inverse thereof being designed to affect application of a force from the removable dental positioning appliance directly on a tooth of the patient.

7. The method of claim 6, wherein applying the pattern includes providing a first pattern on a first portion of the dental mold and a second pattern on a second portion of the dental mold.

8. The method of claim 6, wherein applying the pattern to the portion of the dental mold includes applying the pattern formed of repeated elements of one or more of straight lines, curved lines, uniform circumference bumps, and non-uniform circumference bumps.

9. The method of claim 6, wherein applying a material to the dental mold to form the removable dental positioning appliance includes applying the material such that an outer surface of the shell does not include either the pattern or an inverse thereof.

10. The method of claim 6, wherein applying the material comprises applying one material to the dental mold including the portion having the pattern to form the removable dental positioning appliance such that the appliance includes either the pattern or the inverse thereof on the surface of the inner cavities and such that the appliance with the pattern or the inverse thereof is a unitary body formed from the one material.

\* \* \* \* \*